United States Patent
Rynhart et al.

(10) Patent No.: US 6,747,463 B2
(45) Date of Patent: Jun. 8, 2004

(54) MOISTURE METER

(75) Inventors: Alan Rynhart, Delgany (IE); Sean Fallon, Glenageary (IE); James McIlroy, Shankill (IE)

(73) Assignee: Rynhart Research Limited, County Wicklow (IE)

( * ) Notice: Subject to any disclaimer, the term of this patent is extended or adjusted under 35 U.S.C. 154(b) by 48 days.

(21) Appl. No.: 10/173,836

(22) Filed: Jun. 19, 2002

(65) Prior Publication Data

US 2003/0169054 A1 Sep. 11, 2003

(30) Foreign Application Priority Data

Mar. 8, 2002 (IE) .............................. 2002/0179

(51) Int. Cl.⁷ .............................................. G01R 27/26
(52) U.S. Cl. ...................................... 324/664; 324/658
(58) Field of Search ............................ 73/73; 324/664, 324/689, 694, 722, 658; 340/604

(56) References Cited

U.S. PATENT DOCUMENTS

| | | | | | |
|---|---|---|---|---|---|
| 4,408,128 A | * | 10/1983 | Fujita | .......................... | 324/694 |
| 4,896,795 A | * | 1/1990 | Ediger et al. | .................. | 222/63 |
| 5,422,276 A | * | 6/1995 | Colvin | ........................... | 436/1 |
| 5,491,092 A | * | 2/1996 | Colvin | ........................... | 436/1 |
| 5,621,669 A | * | 4/1997 | Bjornsson | ..................... | 702/85 |
| 6,340,892 B1 | * | 1/2002 | Rynhart et al. | ............. | 324/640 |
| 6,553,813 B2 | * | 4/2003 | Rynhart et al. | ................. | 73/73 |
| 6,637,259 B2 | * | 10/2003 | McElhaney et al. | ........... | 73/73 |
| 6,657,443 B2 | * | 12/2003 | Anderson | .................... | 324/664 |

FOREIGN PATENT DOCUMENTS

| | | |
|---|---|---|
| GB | 2190203 A | 11/1987 |
| GB | 2347220 A | 8/2000 |
| KR | 9401280 B | 2/1994 |

\* cited by examiner

Primary Examiner—N. Le
Assistant Examiner—Walter Benson
(74) Attorney, Agent, or Firm—Jacobson Holman PLLC

(57) ABSTRACT

A moisture meter (1) has a capacitive sensing circuit (11-16) feeding into a digital control circuit having a microcontroller (17). Input buttons (20, 22, 23) allow a user to select a material being surveyed. They also allow the user to instruct the meter (1) to hold a particular reading. This allows it to be more conveniently read. The output of the digital control circuit is fed via an ADC (18) to a moving coil meter (4). This provides an easy-to-read display in which trends as the meter (1) is moved across a surface are easy to track.

13 Claims, 3 Drawing Sheets

MOISTURE METER

INTRODUCTION

1. Field of the Invention

The invention relates to a moisture meter.

2. Prior Art Discussion

Our prior published British Patent Application No. GB2347220A describes a moisture meter which has a digital control circuit driving an LED output display. This meter has many advantageous features such as storage of readings and upload to a host computer, and choice of a range of different materials having different response characteristics.

In using a moisture meter for surveying a building it is desirable to hold the meter or probe against a wall or other surface and to move it across the surface. In this way the surveyor can see the trend in moisture readings as the meter moves from a dry to a wet part of a wall or other surface, and can survey the extent of the dampness and the size of the problem.

Use of a meter of the above type presents problems for surveyors as it is difficult to track trends on the display as the meter is moved. Very often the surveyor sees tumbling digits on the display, and not a clearly visible trend.

Another disadvantage of currently available moisture meters is that for some applications user interaction is complex.

A disadvantage of some analogue moisture meters is that in some applications the measuring locations are difficult to access and the operator may have to hold the meter out of sight while taking a measurement. The scale reading may change if the meter is then moved to a position where the scale can be read.

The invention is therefore directed towards providing a moisture meter to address these problems.

SUMMARY OF THE INVENTION

According to the invention, there is provided a moisture meter comprising:

a moisture sensor;

a digital control circuit comprising means for processing output signals from said sensor and for generating and storing moisture measurements; and an output interface comprising a digital to analogue converter (DAC) connected to the digital control circuit, and an analogue display device comprising means for providing an analogue moisture display in response to outputs of the digital to analogue converter.

In one embodiment, the analogue display device comprises a moving coil meter.

In another embodiment, the moisture meter comprises means for linearising moisture readings.

In a further embodiment, the linearising means comprises a logarithmic amplifier in the sensor.

In one embodiment, the logarithmic amplifier is connected between a sensor amplifier and an analogue to digital converter (ADC) of the digital control circuit.

In another embodiment, the digital control circuit comprises an input interface comprising means for allowing user selection of a desired material.

In a further embodiment, the input interface comprises a user button for selecting a material.

In one embodiment, the digital control circuit comprises means for generating an interrupt upon user selection of a material.

In another embodiment, the digital control circuit comprises means for storing a flag indicating the selected material when the moisture meter is powered down, and for activating with the same material at power-up.

In a further embodiment, the digital control circuit comprises means for locking to a current reading in response to user selection of a hold function at the input interface.

In one embodiment, the digital control circuit comprises means for generating an interrupt upon user selection of the hold function.

In another embodiment, the digital control circuit comprises means for operating in timed loops of monitoring sensor signals, processing the signals, and outputting a moisture reading.

In a further embodiment, the digital control circuit comprises means for powering-down to a sleep mode after expiry of a timeout period for a single reading.

In one embodiment, the digital control circuit comprises means for activating a timer when a timed processing loop generates the same reading as that for the previous processing loop, whereby the timeout period is calculated from the time at which a reading has not changed.

DETAILED DESCRIPTION OF THE INVENTION

BRIEF DESCRIPTION OF THE DRAWINGS

The invention will be more clearly understood from the following description of some embodiments thereof, given by way of example only with reference to the accompanying drawings in which.

DESCRIPTION OF THE EMBODIMENTS

Figure 1:
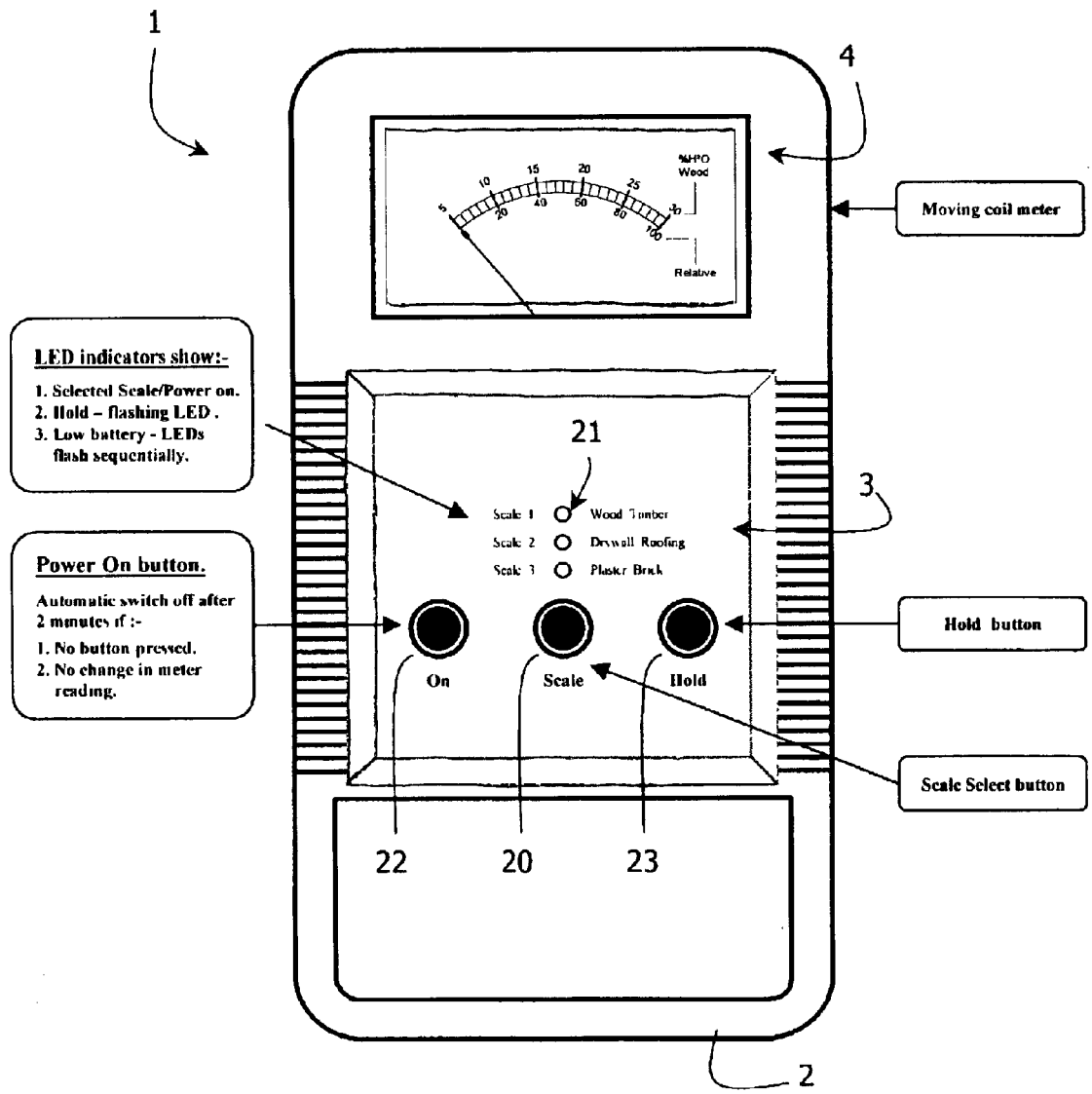
FIG. 1 is a front view of a moisture meter of the invention.
Figure 2:
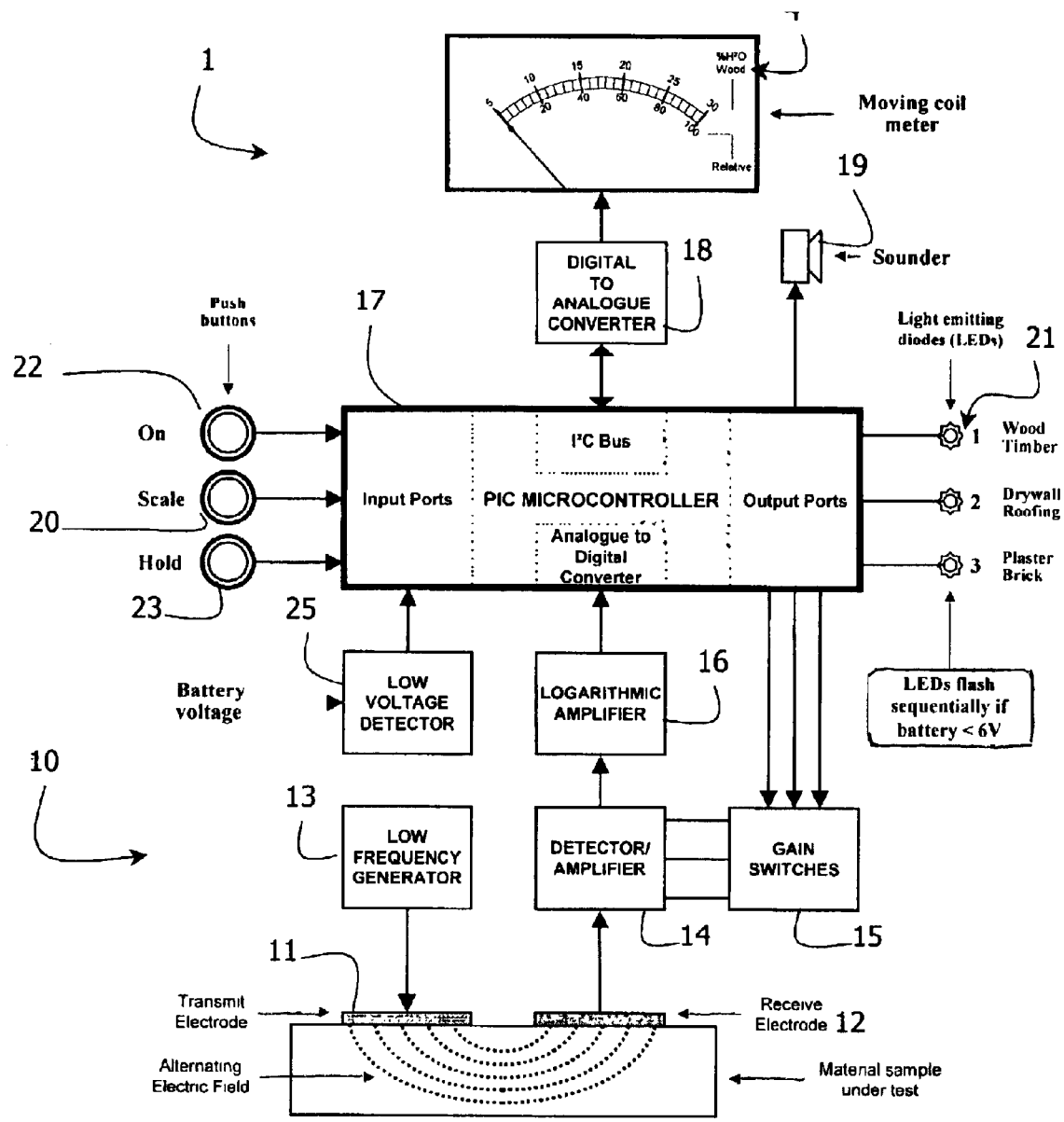
FIG. 2 is a schematic diagram showing construction of the meter in more detail.

Referring to FIG. 1, a moisture meter 1 comprises a hand-held plastics housing 2, an input interface 3, and a moving coil meter display 4. The meter 1 is shown in more detail in FIG. 2.

A sensor 10 comprises a transmit electrode 11, a receive electrode 12, a low frequency generator 13 driving the transmit electrode 11, and a detector/amplifier 14 connected to the receive electrode 12. Gain switches 15 are used to set the scale, in this embodiment (1) wood, (2) drywall or roofing, and (3) plaster or brick. Referring again to FIG. 1 user pressing of a Scale button 20 moves the scale selection between these three, and an LED 21 is activated to indicate the selection.

Finally, the sensor 10 comprises a logarithmic amplifier 16 which linearises the sensor output to provide a linear analogue sensor signal to a digital control circuit. The digital control circuit comprises a PIC microcontroller 17 connected to:

the Scale button 20, an On button 22, and a Hold button 23, the LEDs 21, a DAC (digital to analogue converter) 18, and a sounder 19.

The DAC 18 drives the moving coil meter 4.

The microcontroller 17 controls/processes all instrument functions and operations. It also includes an 8-bit analogue to digital (A/D) converter which converts the analogue moisture readings obtained from the capacitive sensor/logarithmic amplifier chain to digital. As it outputs an 8-bit word, it provides for 256 quantum steps and hence an accuracy of better than 1%. The digitised readings are mathematically processed and then outputted as serial data via a two-wire Inter Integrated Circuit ($I^2C$) bus to the digital to analogue (D/A) converter integrated circuit (IC) 18 which drives the moving coil meter 4 to display the moisture value. The DAC 18 converts from 8-bit digital back to analogue.

The ON, SCALE and HOLD input ports are configured as interrupt requests, i.e., they have priority over all other microcontroller program operations.

Capacitive Moisture Sensor

The two co-planar conductive rubber electrodes 11 and 12 are mounted on the base of the instrument case. To measure/detect moisture, the electrodes are lightly pressed onto the wood or material sample. The capacitance between the electrodes is governed by the dielectric constant of the wood/material sample, which is in turn dependent on the moisture content of the sample. The low frequency generator circuit provides a constant frequency/constant amplitude 125 KHz unity mark space square wave to drive the transmitter electrode which creates an alternating electric field between the electrodes. This causes a very small AC current flow through the material sample and into the receiving electrode. An operational amplifier IC configured as a precision half wave rectifier/amplifier detects and amplifies the AC current and outputs a voltage which is proportional to the moisture content of the sample. The relationship between the moisture content of the sample and the input current to the detector/amplifier is exponential and consequently, to maintain a reasonable balance between detector sensitivity and dynamic range, it is desirable to alter the amplifier gain to cope with the wide variation in dielectric constant band between wood, wall and roofing materials. This is achieved by using the gain switches 15, which are a triple analogue switch IC to set the amplifier gain. The microcontroller 17 assesses the Scale button 20 input and switches on the gain setting appropriate to selected scale.

Logarithmic Amplifier 16

The purpose of the logarithmic amplifier 16 is to convert the exponentially proportional voltage output of the detector/amplifier 14 to follow a linear relationship with respect to moisture content. An additional benefit is that the entire dynamic range of the detector/amplifier 14 can be used, i.e., the measurement range is increased. Ultimately, this permits the display of the moisture value on the moving coil meter 4 with an extended linear scale, which provides excellent reading accuracy.

Microcontroller 17

The instrument is powered by a 9 volt PP3 size Alkaline primary battery which drives a low drop out (LDO), low quiescent current regulator IC to provide a stabilised 5 volt supply for the microcontroller 17. In the OFF condition, the microcontroller 17 goes into a "sleep" mode and in consequence the total supply current drain is only a few microamps. When the ON button 22 is pressed it interrupts the "sleep" mode and wakes up the microcontroller 17 which then:

1. Switches on the 5 volt supply to all the external circuits.
2. Starts a timer module on a 2 minute supply timeout sequence.
3. Checks a battery low voltage detector 25 input and if low (less than 6 volts) issues a low battery warning by sequentially flashing the three scale LEDs.
4. Looks up the last use settings for the SCALE button 20 and restores these conditions, i.e., sets the detector/amplifier 14 gain and switches on the appropriate LED 21.
5. Looks up the last use setting for the HOLD button 23. If HOLD was selected, the LED is put in a flashing mode and the previously saved meter reading is outputted via the $I^2C$ bus to the D/A converter.
6. Starts a 0.25 second repetitive loop (if not in HOLD) for monitoring and presentation of moisture readings, i.e., A/D conversion, processing and $I^2C$ serial data output to the D/A converter.
7. Compares current and previous readings every 0.25 seconds. If readings show change above a preset differential value, the 2 minute supply timeout sequence is restarted.
8. Checks moisture value during each loop and if it exceeds 50 (on the relative meter scale) commences the audible bleep alarm on the sounder.
9. Services any button press (interrupt request) and restarts 2 minute supply timeout sequence.
10. Monitors status of timeout counter, issues double bleep warning at −10 seconds and, at 0 seconds, closes down all operations and puts microcontroller in "sleep" mode.

It will be appreciated that the meter 1 has the advantages of digital circuitry such as the ability to store readings, but can also indicate a moisture trend. The linear output of the logarithmic amplifier 16 allows all ranges for different materials, to be read on one linear scale. This avoids the inconvenience of multiple scales and the danger of taking a reading on a wrong scale.

The digital circuit provides a number of very useful features, including the ability to store a reading until it can accurately read or recorded, an improved range from 5 to 30% moisture content, push button scale selection, and power supply timeout. For example, range changing can be done by push button instead of a switch. In an analogue instrument having a number of different scales and a suppressed zero for timber (5–30%) potentiometers are required to adjust the zero point whereas with the PIC controller 17 can do this arithmetically.

The advantages of signal storage include, for example the storing and display of the last reading after a timeout of the power supply, the extending of the timeout period if the reading changes or a button is pressed. There is also an audible warning of a high reading.

The advantages include the ability to take measurements at measuring locations which are difficult to access and the operator may have to hold the meter out of sight while taking a measurement. The scale reading may change if the meter is then moved to a position where the scale can be read. With storage of measurements the hold button can be pressed and the meter moved to a position where the scale can be read without parallax errors.

It will be appreciated that the meter 1 has a large moving coil meter with a linear scale for all materials by virtue of the gain switches 15 and the logarithmic amplifier to linearise capacitive sensor output. The wood moisture measurement range is 5–30%, as compared with a range of 10–20% for prior analogue meters. The three simple pushbutton controls, ON, SCALE and HOLD allow easy and simple operation SCALE button selects: (1) Wood/Timber, (2) Drywall/Roofing, (3) Plaster/Brick, scales. The three LEDs (light emitting diodes) show the selected scale, indicate if HOLD is selected, and provide a warning of battery nearing end of useful life. The HOLD button freezes the moving coil meter reading, and the selected scale LED flashes to indicate HOLD is in operation. The automatic supply timeout (2 minutes) conserves battery life and the supply timeout is automatically extended if a change in meter reading is detected or if any button is pressed. The meter 1 also provides a 10 second bleep warning on the sounder 19 prior to end of the supply timeout period. The last used scale is memorised at supply timeout and is automatically selected the next time ON button is pressed. If HOLD was selected prior to supply timeout, the frozen meter reading is digitally memorised and restored next time ON button is pressed.

Figure 3:
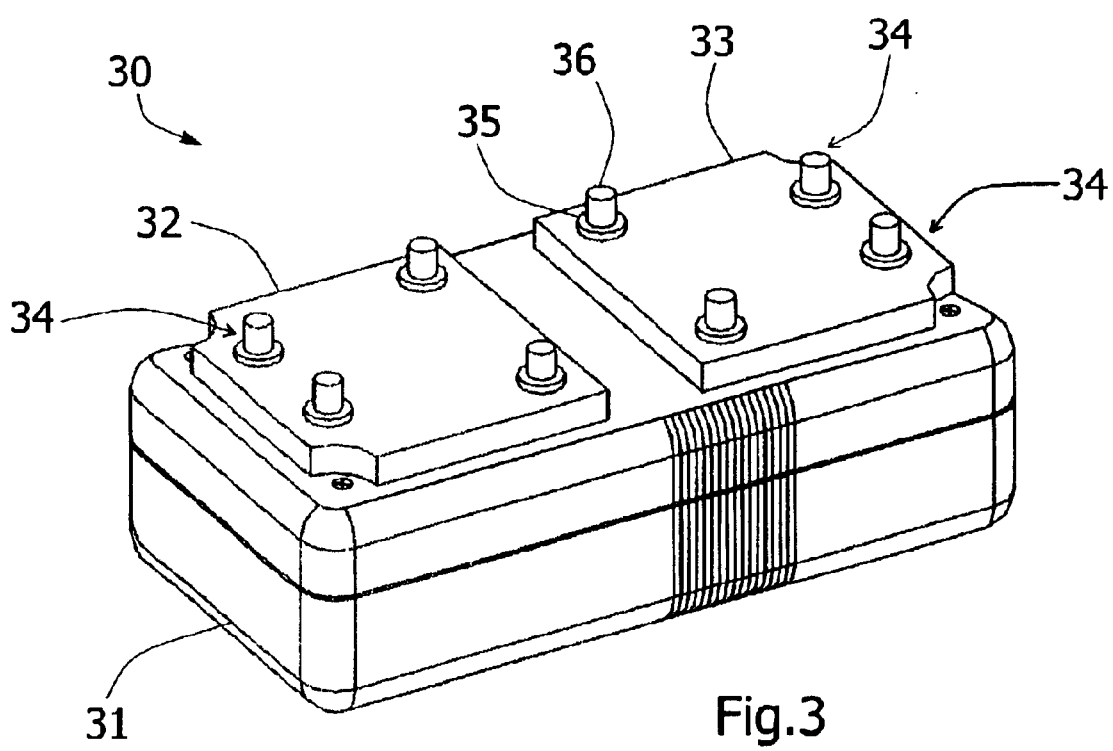
FIG. 3 is a rear perspective view of an alternative moisture meter of the invention.

Referring to FIG. 3 an alternative moisture meter 30 is illustrated. The meter 30 has similar processing circuitry, however its housing 31 supports conductive rubber pads 32 and 33, which in turn each support four spring-loaded contact pins 34 including bases 35 and pin members 36. This contact arrangement is particularly effective for concrete moisture measurement.

The invention is not limited to the embodiments described but may be varied in construction and detail.

What is claimed is:

1. A moisture meter comprising:

a hand-held housing on which are mounted a user input interface, a user output interface, and a moisture sensor for sensing moisture in a solid material upon contact with the solid material;

a digital control circuit within the housing for processing output signals from said moisture sensor and for generating and storing moisture measurements; and the output interface comprising a digital to analogue converter (DAC) connected to the digital control circuit, and an analogue display device for providing an analogue moisture display indicating a moisture trend in response to outputs of the digital to analogue converter, wherein the input interface allows user selection of a hold function, and the digital control circuit locks a current reading in response to user selection of the hold function at the input interface.

2. The moisture meter as claimed in claim 1, wherein the analogue display device comprises a moving coil meter.

3. The moisture meter as claimed in claim 1, wherein the moisture meter comprises means for linearising moisture readings.

4. The moisture meter as claimed in claim 3, wherein the linearising means comprises a logarithmic amplifier in the sensor.

5. The moisture meter as claimed in claim 4, wherein the logarithmic amplifier is connected between a sensor amplifier and an analogue to digital converter (ADC) of the digital control circuit.

6. The moisture meter as claimed in claim 1, wherein the digital control circuit comprises an input interface comprising means for allowing user selection of a desired material.

7. The moisture meter as claimed in claim 6, wherein the input interface comprises a user button for selecting a material.

8. The moisture meter as claimed in claim 6, wherein the digital control circuit comprises means for generating an interrupt upon user selection of a material.

9. The moisture meter as claimed in claim 6, wherein the digital control circuit comprises means for storing a flag indicating the selected material when the moisture meter is powered down, and for activating with the same material at power-up.

10. The moisture meter as claimed in claim 1, wherein the digital control circuit comprises means for generating an interrupt upon user selection of the hold function.

11. The moisture meter as claimed in claim 1, wherein the digital control circuit comprises means for operating in timed loops of monitoring sensor signals, processing the signals, and outputting a moisture reading.

12. A The moisture meter as claimed in claim 1, wherein the digital control circuit comprises means for powering-down to a sleep mode after expiry of a timeout period for a single reading.

13. The moisture meter as claimed in claim 12, wherein the digital control circuit comprises means for activating a timer when a timed processing loop generates the same reading as that for the previous processing loop, whereby the timeout period is calculated from the time at which a reading has not changed.

* * * * *